(12) United States Patent
Behr et al.

(10) Patent No.: US 6,953,606 B2
(45) Date of Patent: Oct. 11, 2005

(54) PERFLUOROALKYL HALOALKYL ETHERS AND COMPOSITIONS AND APPLICATIONS THEREOF

(75) Inventors: Frederick E. Behr, Woodbury, MN (US); Richard M. Flynn, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 22 days.

(21) Appl. No.: 10/689,110

(22) Filed: Oct. 20, 2003

(65) Prior Publication Data

US 2004/0086650 A1 May 6, 2004

Related U.S. Application Data

(62) Division of application No. 09/231,203, filed on Jan. 14, 1999, now Pat. No. 6,653,512, which is a division of application No. 08/931,105, filed on Sep. 15, 1997, now Pat. No. 6,552,090.

(51) Int. Cl.$^7$ ................................................. B05D 1/00
(52) U.S. Cl. ........................ 427/384; 510/175; 510/276; 568/583
(58) Field of Search .......................... 568/583; 510/175, 510/276; 427/384

(56) References Cited

U.S. PATENT DOCUMENTS

| | | |
|---|---|---|
| 3,453,333 A | 7/1969 | Litt et al. |
| 3,549,711 A | 12/1970 | Merrill et al. |
| 3,778,381 A | 12/1973 | Rosano et al. |
| 3,900,372 A | 8/1975 | Childs et al. |
| 3,903,012 A | 9/1975 | Brandreth |
| 3,962,460 A | 6/1976 | Croix et al. |
| 5,125,978 A | 6/1992 | Flynn et al. |
| 5,275,669 A | 1/1994 | Van Der Puy et al. |
| 5,300,253 A | 4/1994 | Buchwald et al. |
| 5,466,877 A | 11/1995 | Moore |
| 5,476,974 A | 12/1995 | Moore et al. |
| 5,550,273 A | 8/1996 | Savu |
| 5,658,962 A | 8/1997 | Moore et al. |
| 5,660,888 A | 8/1997 | Grenfell et al. |
| 5,750,797 A | 5/1998 | Vitcak et al. |
| 5,839,311 A | 11/1998 | Grenfell et al. |
| 5,962,390 A | * 10/1999 | Flynn et al. ................. 510/286 |
| 6,043,201 A | * 3/2000 | Milbrath et al. ............ 508/582 |

FOREIGN PATENT DOCUMENTS

| | | |
|---|---|---|
| DE | 1 294 949 | 5/1969 |
| DE | 16 43 992 | 6/1971 |
| EP | 0 450 855 A2 | 10/1991 |
| FR | 2 287432 | 7/1976 |
| WO | WO 93/11280 | 6/1993 |
| WO | WO 96/22356 | 7/1996 |
| WO | WO 97/22683 | 6/1997 |
| WO | WO 98/12287 | 3/1998 |

OTHER PUBLICATIONS

B.N. Ellis, "Cleaning and Contamination of Electronics Components and Assemblies", Electrochemical Publications, Ltd., (1986), pp. 182–195.

H. Finkelstein, Berichte, (1910), pp. 1528–1533, vol. 43.

Smith et al., "The Chemistry of Carbonyl Fluoride. II. Synthesis of Perfluoroisopropyl Ketones", *J. Am. Chem. Soc.*, (Nov. 20, 1962), pp. 4285–4288, vol. 84.

Wang et al., "Apparent Molar Volume and Apparent Molar Adiabatic Compressibility Studies of Anesthetic Molecules in Aqueous Micelle Solutions of CTAB and CTAC as a Function of Surfactant Concentration and Temperature," J. Phys. Chem, (1994), pp. 4368–4374, vol. 98.

Yamashita et al., "Development of CFC Alternatives Containing Oxygen Atom," International Conference on CFC and BFC (Halons), (Aug. 7–10, 1994), pp. 55–69, Shanghai, China.

P.S. Zurer, "Looming Ban on Production of CFCs, Halons Spurs Switch to Substitutes", Chemical & Engineering News, (Nov. 15, 1993), pp. 12–18.

* cited by examiner

Primary Examiner—Erma Cameron
(74) Attorney, Agent, or Firm—Kent S. Kokko

(57) ABSTRACT

Described are compositions comprising perfluoroalkyl haloalkyl ethers and, optionally, surfactant; uses for perfluoroalkyl haloalkyl ether compounds and compositions thereof, optionally comprising surfactant; and perfluoroalkyl haloalkyl ethers.

9 Claims, No Drawings

PERFLUOROALKYL HALOALKYL ETHERS AND COMPOSITIONS AND APPLICATIONS THEREOF

CROSS-REFERENCE TO RELATED APPLICATION

This is a divisional of application Ser. No. 09/231,203, filed Jan. 14, 1999, now U.S. Pat. No. 6,653,512 which is a divisional of U.S. Ser. No. 08/931,105, filed Sep. 15, 1997, issued as U.S. Pat. No. 6,552,090.

The present invention relates to perfluoroalkyl haloalkyl ether compounds, to compositions containing such compounds, and to the use of such compounds and compositions.

BACKGROUND

Chlorinated chemicals (e.g., chlorofluorocarbons, and hydrochlorofluorocarbons) have been used in the past as solvents within a number of specialized industrial applications. For instance, chlorinated chemicals are known to be useful within cleaning applications, including dry cleaning, wherein contaminated articles are washed (e.g., immersed in or otherwise contacted) to remove the contaminant. The chlorinated chemicals can be used as liquids or vapors, and at ambient or elevated temperatures (often in cleaning applications accompanied by ultrasonic agitation). Other applications wherein chlorinated chemicals are known to be useful include using chlorinated chemicals as coating or deposition solvents, for the removal of water from substrates, as a thermal media for heat transfer applications, as a blowing agent for polymeric foams, as a fire-extinguishing agent, and as a coolant/lubricant in metal working applications.

A major concern relating to the use of such chlorinated chemicals is the tendency (especially when used at an elevated temperature) for vapor loss into the atmosphere, causing pollution. Although care can be exercised to minimize such losses (e.g., through good equipment design and vapor recovery systems), most practical applications result in the loss of at least some vapor into the atmosphere.

Popular chlorinated chemicals that have been useful in the past (e.g., as cleaning solvents) include 1,1,2-trichloro-1,2, 2-trifluoroethane and 1,1,1-trichloroethane. These are useful alone or in admixture with one or more co-solvents such as aliphatic alcohols or other low molecular weight polar compounds. These particular chlorinated compounds were initially believed to be environmentally benign, but have now been linked to depletion of the earth's ozone. According to the Montreal Protocol and its attendant amendments, production of such solvents has been discontinued in the U.S. (see, e.g., P. S. Zurer, "Looming Ban on Production of CFCs, Halons Spurs Switch to Substitutes," Chemical & Engineering News, page 12, Nov. 15, 1993).

Thus, there has developed a need for substitutes or replacements for chlorinated chemicals that have been commonly used in the past. Such substitutes should exhibit one or more useful chemical or physical properties including a low ozone depletion potential, a boiling range suitable for solvent cleaning applications, and high solvency, i.e., the ability to readily dissolve or disperse organic and/or inorganic contaminants, such as water, hydrocarbon-based compounds, and fluorocarbon-based compounds. Preferably, substitutes will also be low in toxicity, have no measurable flash points (as determined by ASTM D3278-89), have acceptable thermal and chemical stability for use in a given application, and have short atmospheric lifetimes and low global warming potentials. Many compounds have been proposed as substitutes for such chlorinated compounds in a number of different uses and applications. Still, there remains a need for chemical compounds capable of replacing past commonly used chlorinated compounds and that exhibit one or more of such useful chemical or physical properties.

SUMMARY OF THE INVENTION

Perfluoroalkyl haloalkyl ether compounds have been discovered which can be useful by themselves and in chemical compositions for purposes including but not limited to use as solvents e.g., in cleaning processes such as dry cleaning processes, water removal processes, and in coating processes. The ethers have a haloalkyl component and a perfluorinated alkyl component, and exhibit useful and advantageous properties. These perfluoroalkyl haloalkyl ethers can exhibit, for example, one or more of the following physical or chemical properties: useful boiling points, high solvency, acceptable toxicity properties, chemical and thermal stability, low ozone depletion characteristics, and preferably, substantially no flash point. Additionally, the presence of at least one hydrogen on the haloalkyl component allows for degradation of the compound, and reduces its long-term presence in the atmosphere.

An aspect of the invention relates to a chemical composition containing a perfluoroalkyl haloalkyl ether compound and a surfactant. The perfluoroalkyl haloalkyl compound can be described generally by the formula:

wherein $R_f$ is perfluoroalkyl and $R_x$ is haloalkyl. Preferred such compounds include those of the formula:

wherein $R_f$ is a perfluoroalkyl preferably having at least about 3 carbons, most preferably from about 3 to 15 carbons, and optionally containing a catenary heteroatom such as N or O; x preferably is from about 1 to 6; y is at least one; w is in the range from 0 to about 2, X is a halogen chosen from bromine, iodine, and chlorine; z is at least one; and w+y+z is equal to 2x+1.

Another aspect of the invention relates to a process for removing contaminants from a substrate. The process includes the step of contacting the substrate with a composition comprising a perfluoroalkyl haloalkyl ether. The perfluoroalkyl haloalkyl ether can be of the formula:

wherein $R_f$ is perfluoroalkyl and $R_x$ is haloalkyl. Preferred such compounds include those of the formula:

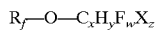

wherein $R_f$ is a perfluoroalkyl preferably having at least about 3 carbons, most preferably from about 3 to 15 carbons, and optionally containing a catenary heteroatom such as N or O; x is from about 1 to 6; y is at least one; w is in the range from 0 to about 2, X is a halogen chosen from bromine, iodine, and chlorine; z is at least one; and w+y+z is equal to 2x+1.

Yet another aspect of the invention relates to perfluoroalkyl haloalkyl ethers, including $n\text{-}C_3F_7OCH_2Cl$, $n\text{-}C_3F_7OCHCl_2$, and those of the general formula:

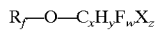

wherein $R_f$ is a perfluoroalkyl having at least 4 carbons and optionally containing a catenary heteroatom such as N or O; x is preferably from 1 to 2; y is at least one; w can be in the range from 0 to about 2, X is a halogen chosen from bromine, iodine, and chlorine; z is at least one; and w+y+z is equal to 2x+1. Specific such perfluoroalkyl haloalkyl ether compounds include those of the formulas c-$C_6F_{11}OC_xH_yF_wX_z$, c-$C_6F_{11}CF_2OC_xH_yF_wX_z$, and $C_4F_9OC_xH_yF_wX_z$; specific compounds include $C_4F_9OCH_2Cl$, $C_4F_9OCHCl_2$, $C_4F_9OCH_2Br$, $C_4F_9OCH_2I$, $C_4F_9OCHClCH_3$, and $C_4F_9OCH_2CH_2Cl$.

Yet another aspect of the invention relates to perfluoroalkyl haloalkyl ethers wherein the perfluoroalkyl component comprises a catenary nitrogen; i.e., wherein the perfluoroalkyl component comprises a perfluorinated amine. Ether-containing perfluorinated amines can be generally described by the formula:

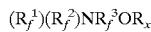

wherein $R_x$ is a haloalkyl; $R_f^1$ and $R_f^2$ are independently straight or branched perfluoroalkyl groups preferably having from 1 to 6 carbons, or are independently straight or branched perfluoroalkylene groups preferably having from 2 to about 4 carbons, the perfluoroalkylene groups being bonded to each other to form a ring, and $R_f^3$ is a linear or branched perfluoroalkylene preferably having from about 1 to 6 carbon atoms, wherein $R_f^1$, $R_f^2$ and $R_f^3$ can optionally (and independently) contain one or more catenary heteroatoms. Preferably $R_f^1$ and $R_f^2$, when perfluoroalkyl, have from 1 to about 3 carbon atoms, and when perfluoroalkylene have from 2 to 3 carbon atoms; $R_f^3$ preferably has from 1 to about 3 carbon atom. Also preferably, $R_x$ contains from 1 to about 6 carbons, more preferably from about 1 to 2 carbons.

As used within the present description when referring to the claimed perfluoroalkyl haloalkyl ethers, terms will be given the following meanings:

"haloalkyl" refers to an alkyl radical wherein at least one of the alkyl hydrogens has been replaced with a halogen chosen from chlorine, bromine, or iodine;

"perfluoro-" refers to chemical groups such as alkyl groups in which essentially all of the carbon-bonded hydrogen has been replaced by fluorine. Perfluorinated compounds such as perfluoroalkyl groups are generally the product of a fluorination process (e.g. electrochemical fluorination using, for example anhydrous HF as a source of fluorine, or direct fluorination using elemental fluorine) and typically comprise a mixture of one or more perfluoroalkyl isomers and one or more hydride-containing compounds due to incomplete replacement of hydrogen by fluorine. Minor amounts (e.g., less than 5%, or less than 1% by weight) of such residual hydride content in the perfluoroalkyl groups are therefore within this definition.

DETAILED DESCRIPTION

Compounds of the invention include ether compounds having a perfluoroalkyl component and a haloalkyl component, compounds also referred to as perfluoroalkyl haloalkyl ethers (also referred to herein as "the ether" or "the ethers"). These perfluoroalkyl haloalkyl ethers can generally be described by the formula:

wherein $R_f$ is perfluoroalkyl and $R_x$ is haloalkyl.

Preferably, the ethers can exhibit one or more useful chemical and physical properties including a boiling point in the range from about 25° C. to about 200° C., more preferably from about 25° C. to about 125° C.; essentially no measurable flash point as determined by ASTM D3278-89; acceptable toxicological properties; and high solvency.

The perfluorinated component $R_f$ can be any perfluorinated group able to provide a perfluoroalkyl haloalkyl ether with one or more useful chemical or physical properties as defined herein. Useful $R_f$ groups are described, for example, in Assignee's copending U.S. Pat. No. 5,962,390, and incorporated herein by reference. The $R_f$ group can be linear, branched, cyclic, or any combination thereof, and can optionally contain one or more catenary heteroatoms such as oxygen or nitrogen. Examples of preferred $R_f$ groups include linear or branched perfluoroalkyls having from 3 to about 15 carbons, and perfluorocycloalkyl-containing perfluoroalkyls having from 5 to about 15 carbons. $R_f$ groups containing a perfluorocycloalkyl group can optionally contain one or more substituents, e.g., one or more perfluoroalkyl, the substituent preferably having from 1 to about 4 carbons.

Examples of $R_f$ groups comprising a catenary heteroatom include perfluoroamine groups. Preferred perfluoroamine groups include those represented by the formula

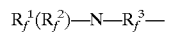

wherein $R_f^1$ and $R_f^2$ are independently straight or branched perfluoroalkyl groups preferably having from about 1 to 6 carbons, or are independently straight or branched perfluoroalkylene groups preferably having from about 2 to 4 carbons, the perfluoroalkylene groups being bonded to each other to form a ring; $R_f^3$ is a linear or branched perfluoroalkylene having from about 1 to 6 carbon atoms; and wherein $R_f^1$, $R_f^2$ and $R_f^3$ can optionally (and independently) contain one or more catenary heteroatoms.

Most preferably, $R_f$ can be a linear or branched perfluoroalkyl group having from 3 to about 10 carbons, a perfluorocycloalkyl-containing perfluoroalkyl group having from 5 to about 10 carbons, a perfluorocycloalkyl group having from about 5 to 6 carbons, or a perfluoroamine group having from 4 to 11 carbons. Perfluorocycloalkyl groups can optionally and preferably be substituted with perfluoroalkyl groups, e.g., with one or more perfluoromethyl groups Non-limiting examples of $R_f$ groups include the following:

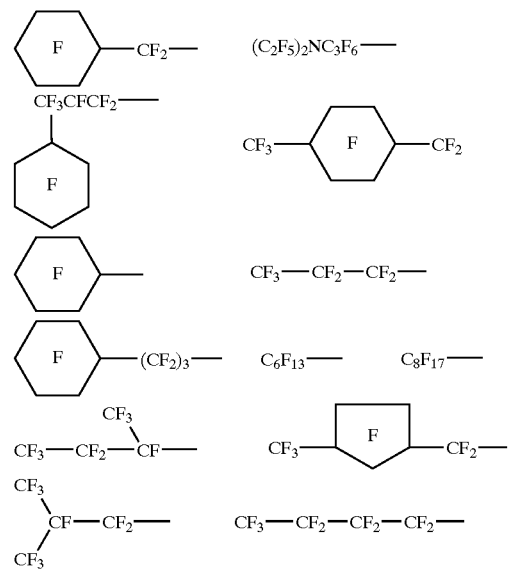

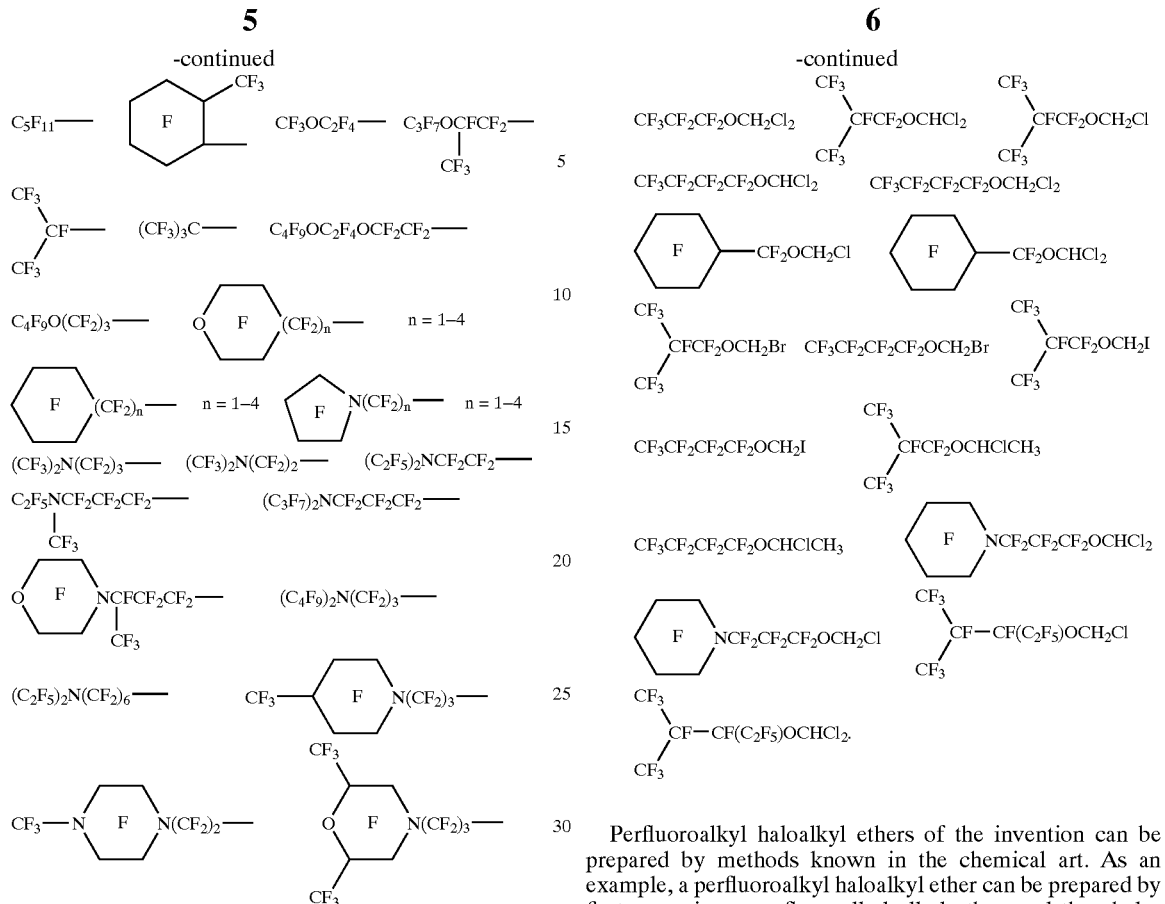

The haloalkyl component, $R_x$, of the perfluoroalkyl haloalkyl ether can be any alkyl group substituted with at least one halogen chosen from chlorine, iodine, or bromine, and at least one hydrogen. Optionally, the haloalkyl group can also contain one or more fluorines, e.g., from 0 to about 2 fluorines. Preferred haloalkyls include those of the formula:

wherein x is preferably in the range from about 1 to 6, more preferably from about 1 to 2; y is at least 1; w is preferably in the range from 0 to about 2; X is a halogen chosen from bromine, iodine, and chlorine; z is at least one; and w+y+z equals 2x+1.

Preferred perfluoroalkyl haloalkyl ethers include those described by the formula:

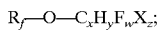

wherein $R_f$, X, H, Y, W, X, and Z are as defined.

Specific such perfluoroalkyl haloalkyl compounds include:

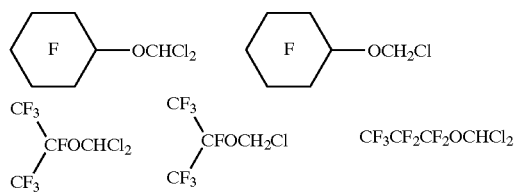

Perfluoroalkyl haloalkyl ethers of the invention can be prepared by methods known in the chemical art. As an example, a perfluoroalkyl haloalkyl ether can be prepared by first preparing a perfluoroalkyl alkyl ether, and then halogenating the alkyl component to produce a desired perfluoroalkyl haloalkyl ether. Perfluoroalkyl alkyl ethers can be prepared by a number of chemical synthesis methods generally known and described in the chemical art. For example, perfluoroalkyl alkyl ethers can be prepared by alkylation of perfluorinated alkoxides prepared by the reaction of a perfluoro acyl halide (e.g., perfluorinated acyl fluoride or perfluoro acyl chloride), a perfluoroketone, a perfluoro ester, a perfluoro carbonate or a perfluorocarboxylic acid anhydride, with an anhydrous alkali metal fluoride (e.g., potassium fluoride or cesium fluoride) or anhydrous silver fluoride in an anhydrous, polar, aprotic solvent See, e.g., U.S. Pat. No. 3,549,711 (Merrill); U.S. Pat. Nos. 6,380,419 and 5,750,797.

According to one reaction scheme, a perfluoro acyl fluoride is treated with an anhydrous alkali metal fluoride in an anhydrous, polar, aprotic solvent to generate an intermediate perfluoroalkoxide which is alkylated to produce a perfluoroalkyl alkyl ether.

In this scheme, $R_f'CF_2$ corresponds to Rf as defined above. If desired, a perfluoro acyl chloride, perfluorocarboxylic acid anhydride, perfluoro ester, or perfluoro carbonate may be substituted for the fluoride. R $X^1$ is an alkylating agent wherein R is a hydrocarbon which can be halogenated to produce the above-defined haloalkyl $R_x$, and $X^1$ is a leaving group which can be, for example, an alkylsulfate, alkyl fluorosulfate, a halide, alkyl sulfonate or alkyl tosylate. Examples of suitable alkylating agents include dialkyl sulfates (e.g., dimethyl sulfate), alkyl halides (e.g., methyl iodide), alkyl p-toluenesulfonates (e.g., methyl p-toluenesulfonate), alkyl perfluoroalkanesulfonates (e.g., methyl perfluoromethanesulfonate), methyl fluorosulfate, and the like.

In a second reaction scheme, a perfluoroketone can be converted to a desired perfluoroalkyl alkyl ether. The perfluoroketone is reacted with anhydrous alkali metal fluoride to generate an intermediate secondary perfluoroalkoxide which is alkylated to produce a perfluoroalkyl alkyl ether.

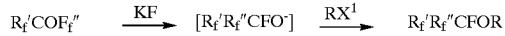

In this scheme R—$X^1$ is as defined, and $R_f'$ and $R_f''$ are independently perfluoroalkyl groups such that $R_f'$ and $R_f''$ preferably have in combination 3 to 15 carbons. $R_f'R_f''CF$ corresponds to $R_f$ as defined.

Alternatively, a fluorinated tertiary alcohol can be allowed to react with a base, e.g., potassium hydroxide or sodium hydride, to produce a perfluorinated tertiary alkoxide which can then be alkylated by reaction with alkylating agent.

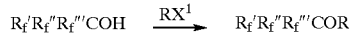

In this scheme R—$X^1$ is as defined, and $R_f'$, $R_f''$, and $R_f'''$ are independently perfluoroalkyl groups such that $R_f'$, $R_f''$, and $R_f'''$ preferably have in combination, 3 to 15 carbons. $R_f'R_f''R_f'''C$ corresponds to $R_f$ as defined.

Suitable anhydrous, polar, aprotic solvents for use in the above reaction schemes include acyclic ethers such as diethyl ether, ethylene glycol dimethyl ether, and diethylene glycol dimethyl ether; carboxylic acid esters such as methyl formate, ethyl formate, methyl acetate, diethyl carbonate, propylene carbonate, and ethylene carbonate; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof.

Perfluorinated acyl fluorides can be prepared by electrochemical fluorination of the corresponding hydrocarbon carboxylic acid (or a derivative thereof), using either anhydrous hydrogen fluoride (Simons ECF) or KF.2HF (Phillips ECF) as the electrolyte. Such methods are known in the fluorochemical art. Perfluorinated acyl fluorides and perfluorinated ketones can also be prepared by dissociation of perfluorinated carboxylic acid esters which can be prepared from the corresponding hydrocarbon or partially-fluorinated carboxylic acid esters by direct fluorination with fluorine gas. Dissociation can be achieved by contacting the perfluorinated ester with a source of fluoride ion under reacting conditions (see U.S. Pat. No. 3,900,372 (Childs), the description of which is incorporated herein by reference), or by combining the ester with at least one initiating reagent selected from the group consisting of gaseous, non-hydroxylic nucleophiles; liquid, non-hydroxylic nucleophiles; and mixtures of at least one non-hydroxylic nucleophile (gaseous, liquid, or solid) and at least one solvent which is inert to acylating agents. See also U.S. Pat. No. 5,466,877 (Moore), incorporated herein by reference.

Perfluoroalkyl alkyl ethers can be halogenated, e.g., chlorinated, by methods generally known in the chemical art, to produce a perfluoroalkyl haloalkyl ether. For instance, perfluoroalkyl alkyl ethers can be chlorinated by photochemical methods, by irradiating the perfluoroalkyl alkyl ether with ultraviolet (UV) radiation in the presence of gaseous chlorine. An example of such a reaction shown for i-$C_4F_9OCH_3$, is as follows:

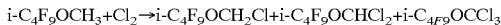

Different amounts of each reaction product will be present depending on a number of factors involved in the reaction, e.g., reaction conditions and relative amounts of each reactant. Such methods are described, for example, in U.S. Pat. No. 3,962,460 (Croix et al.).

According to another halogenation method, chlorination of a perfluoroalkyl alkyl ether can be accomplished using a free radical catalyst such as 2,2-azobisisobutyronitrile (AIBN, available from Aldrich Chemical). In such a system the free radical catalyst is believed to decompose to produce one or more free radicals which react with elemental chlorine to give a chlorine radical (Cl.). The chlorine radical abstracts hydrogen from a perfluoroalkyl alkyl ether to yield an ether radical, which in turn reacts with a molecule of elemental chlorine to yield a new chlorine radical and a molecule of perfluoroalkyl chloroalkyl ether.

The chlorine of a perfluoroalkyl haloalkyl ether can be replaced with a different halogen, e.g., bromine or iodine, to convert the perfluoroalkyl chloroalkyl ether to an analogous perfluoroalkyl bromo- or iodoalkyl ether. Such methods of replacing a chlorine with bromine or iodine are very well known in the organic chemistry art, such as with the Finkelstein reaction, (H. Finkelstein, Ber. 43 1528 (1910)).

The perfluoroalkyl haloalkyl ethers can be useful and can be used either alone or within a chemical composition in admixture with one or more other ethers or other ingredients such as surfactant, co-solvent, or both.

Suitable surfactants include those surfactants that are compatible with (e.g., soluble or dispersible in) the ether to a useful degree. Although the particular surfactant chosen will depend on the desired application, useful surfactants generally will affect one or more of the surface tension, wetting ability, and/or HLB of the composition. In cleaning applications, preferred surfactants can promote removal of a contaminant by dissolving, dispersing or otherwise displacing the contaminant.

One useful class of surfactants includes nonionic surfactants, especially those having a hydrophilic-lipophilic balance (HLB) of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides or carboxamides. Mixtures of surfactants having complementary properties may be used in which one surfactant is added to a cleaning composition to promote oily soil removal and another added to promote water-soluble soil removal.

The surfactant, if used, can be present in a composition in any amount considered to be effective for a desired application. Generally, surfactant can be present in an amount less than about 10 weight percent of the composition, and is preferably present in a range from about 0.1 to 5.0 wt. %, more preferably from about 0.2 to 2.0 wt. % of the composition.

A co-solvent can be included in the composition to modify or enhance the physical or chemical properties of the composition, including solvency and flash point, for a particular use. Useful co-solvents include alcohols, ethers, alkanes including cycloalkanes, alkenes, perfluorocarbons, perfluorinated tertiary amines, perfluoroethers, esters, ketones, aromatics, siloxanes, hydrochlorocarbons, hydrochlorofluorocarbons, and hydrofluorocarbons. Representative specifically useful examples of co-solvents which can be used in combination with the ether within a cleaning composition include methanol, ethanol, isopropanol, t-butyl alcohol, isobutyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, methylcyclopentane, decalin, methyl decanoate, t-butyl acetate, ethyl acetate, diethyl phthalate, 2-butanone, methyl isobutyl ketone, toluene, p-chlorobenzotrifluoride, trifluorotoluene, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, 1,3-bis(trifluoromethyl)benzene, 1,4-bis(trifluoromethyl) benzene, and bromopropane.

Co-solvent can be included in the composition in any useful weight ratio (as defined by the weight of the ether to co-solvent), and can preferably be included in an amount such that the resulting composition exhibits essentially no flash point. Of course the exact amounts of ether and co-solvent will depend on many factors, including the specific application for which the composition is intended, the identity of each of the ether and the co-solvent, the presence of other ingredients such as a surfactant, etc., and even the operating conditions under which the composition is expected to be used. Still, by way of specific example, preferred cleaning compositions include from about 50 to 99 parts by weight perfluoroalkyl haloalkyl ether per 100 parts by weight of combined ether and co-solvent, with a preferred amount of ether per co-solvent being from about 75 to 99 parts by weight ether per 100 parts by weight of combined ether and co-solvent.

The cleaning process of the invention can be accomplished by contacting a contaminated substrate with the above-described ether or a composition comprising the ether, to disperse, dissolve, or otherwise displace contaminants. As used herein, the term "contaminant" generally refers to any matter contacting a substrate, that can be desirously displaced from the substrate, at least in part, by contact with one or more of the above-identified ethers or a composition containing such ether. For example, contaminants generally include materials such as light hydrocarbon substances; higher molecular weight hydrocarbon substances such as mineral oils and greases; fluorocarbon substances including perfluoropolyethers, bromotrifluoroethylene oligomers (gyroscope fluids), chlorotrifluoroethylene oligomers (hydraulic fluids, lubricants); silicone oils and greases; solder fluxes; particulates; soils, substances, or materials that can accumulate on leather, silk, fabrics as prepared into clothes, and other fiber and textile substrate materials; and other such substances.

The substrate can be of any nature and composition, and can be inorganic or organic. Representative examples of useful substrates include metals; ceramics; glass; polycarbonate; polystyrene; acrylonitrile-butadiene-styrene copolymer; synthetic nonwoven materials; natural fibers (and fabrics derived therefrom) such as cotton, silk, fur, suede, leather, linen, and wool; synthetic fibers (and fabrics) such as polyester, rayon, acrylics, nylon, and blends thereof; fabrics comprising a blend of natural and synthetic fibers; and composites of the foregoing materials.

In a general sense, the cleaning process of the invention is accomplished by contacting a substrate with a composition containing a perfluoroalkyl haloalkyl ether (either alone or in admixture with other ingredients), to displace a contaminant. The composition can be used in either the gaseous or the liquid state (or both), and with any of the known techniques for contacting a substrate to a cleaning composition. For example, a liquid cleaning composition can be sprayed or brushed onto the substrate, a gaseous cleaning composition can be blown across a substrate, or a substrate can be immersed in either a gaseous or a liquid composition. Optionally, elevated temperatures, ultrasonic energy, and/or agitation can be used to facilitate the process. Various different solvent cleaning techniques are described by B. N. Ellis in *Cleaning and Contamination of Electronics Components and Assemblies*, at pages 182–94 (1986).

Specific applications of the process exist wherein certain contaminants can be displaced or cleaned from particular substrates. As a first example, the composition and process can be useful in the precision cleaning of electronic components (e.g., circuit boards), optical or magnetic media, and medical devices. To displace water from a substrate such as a circuit board the cleaning process can be carried out by contacting the surface of the substrate with a liquid cleaning composition which preferably contains a non-ionic surfactant. The wet substrate is immersed in the liquid composition and agitated therein, the displaced water is separated from the liquid composition, and the resulting water-free substrate is removed from the liquid composition. Further description of these types of processes, and the substrates that can be treated, are described in U.S. Pat. No. 5,125,978 (Flynn et al.) and in U.S. Pat. No. 3,903,012 (Brandreth), the descriptions of which are incorporated herein by reference.

As another specific application, the process is particularly useful in the solvent-type processes of cleaning fabric and garments, etc., including the process generally known as dry cleaning. According to such process, contaminants can be removed from fiber and textile substrates. This type of cleaning process can be carried out by contacting the fiber or textile with the composition at ambient or elevated temperatures. The contaminated substrate can be agitated to promote the dissolution, dispersion, or displacement of soil contaminants using any conventional agitation means including shaking, stirring and ultrasonic agitation. When the textile is sufficiently cleaned, the composition may be removed (e.g. by decantation), the textile optionally rinsed using fresh cleaning composition or any conventional dry-cleaning solvent to ensure soil removal and prevent redeposition, and the textile can be dried, for example, by air-drying with or without added heat.

The perfluoroalkyl haloalkyl ethers can be useful not only in cleaning applications, but also in coating deposition, where the ether functions as a carrier for a coating material to enable deposition of the coating material on the surface of a substrate. The invention thus also provides a coating composition and a process for depositing a coating on a substrate surface.

The coating process comprises the step of applying to at least a portion of a coating substrate a coating (e.g., in the form of a film) of a liquid coating composition comprising (a) a perfluoroalkyl haloalkyl ether according to the description above, and (b) at least one coating material which is soluble or dispersible in the composition. The coating composition can further comprise one or more co-dispersants or co-solvents (as defined supra, preferably those having boiling points below about 125° C.) and/or one or more additives (e.g., surfactants, coloring agents, stabilizers, antioxidants, flame retardants, and the like). Preferably, the process further comprises the step of removing the ether and optional co-solvent from the coating by, e.g., allowing evaporation (which can be aided by the application of, e.g., heat or vacuum).

Coating materials which can be deposited by the process include pigments, lubricants, stabilizers, adhesives, antioxidants, dyes, polymers, pharmaceuticals, release agents, inorganic oxides, and the like, and combinations thereof, examples include titanium dioxide, iron oxides, magnesium oxide, perfluoropolyethers, polysiloxanes, stearic acid, acrylic adhesives, polytetrafluoroethylene, amorphous copolymers of tetrafluoroethylene, and combinations thereof. Preferred coating materials include perfluoropolyether, hydrocarbon, and silicone lubricants; amorphous copolymers of tetrafluoroethylene; polytetrafluoroethylene; and combinations thereof.

The coating substrate can be any of the substrates described above for cleaning applications, or it can be any other type of natural or synthetic substrate, e.g., in the form of a film, a non-woven material, or any other material desired to be coated with a coating material. The coating process can be particularly useful for coating magnetic hard disks or electrical connectors with perfluoropolyether lubricants, or medical devices with silicone lubricants.

To form a coating composition the components of the composition (i.e., the ether, the coating material, and any co-dispersant or co-solvent) can be combined by any conventional mixing technique used for dissolving, dispersing, or emulsifying coating materials, e.g., by mechanical agitation, ultrasonic agitation, manual agitation, and the like. The components can be combined in any ratio depending upon the desired thickness of the coating, but the coating material preferably constitute from about 0.1 to about 10 weight percent of the coating composition for most coating applications.

The coating process can be carried out by applying the coating composition to a coating substrate using any conventional technique. For example, the composition can be brushed or sprayed (e.g., as an aerosol) onto the substrate, or the substrate can be spin-coated. Preferably, the substrate is coated by immersion in the composition. Immersion can be carried out at any suitable temperature and can be maintained for any convenient length of time.

EXAMPLES

All compounds prepared have had their structures confirmed by gc-ms and $^1$H and $^{19}$F nmr as appropriate.

Examples 1

Preparation of n-$C_3F_7OCH_2Cl$ and n-$C_3F_7OCHCl_2$

A 500 mL flask equipped with a magnetic stir bar, gas inlet tube, condenser, and thermometer was charged with $C_3F_7OCH_3$ (158 g, 0.79 mole). The flask was illuminated with two fluorescent bulbs (BLAK-RAY™, 254 nm), as an initial aliquot of chlorine gas (~3.5 g) was passed through a gas trap into the flask. After a short initiation period, the evolution of HCl was noted and the temperature slowly increased. A total of 56.1 g (0.79 mole) chlorine was added. When conversion was essentially complete, as measured by gas chromatography, the reaction mixture was washed with aqueous KOH and then brine.

Gas liquid chromatography revealed the following composition of the product mixture: unreacted starting material n-$C_3F_7OCH_3$ (6% area percent), n-$C_3F_7OCH_2Cl$ (66%) and n-$C_3F_7OCHCl_2$ (27%),and n-$C_3F_7OCCl_3$ (1%). Unless otherwise specified, all such chromatography percents are in area percent.

The product mixture was distilled through a concentric tube fractionation unit (available from Ace Glass) to remove the starting material. The residue was then distilled through a 36 inch spinning band distillation column (available through B/R Instrument Corporation) and n-$C_3F_7OCH_2Cl$ (purity of 99.5%, b.r.=59.4–59.8° C.) and n-$C_3F_7OCHCl_2$ (purity of 99.5%, b.p.=67.7° C.) was isolated.

Example 2

Preparation of $C_4F_9OCH_2Cl$ and $C_4F_9OCHCl_2$

Using essentially the procedure of Example 1, $C_4F_9OCH_3$ (701.5 g, 2.81 mole of approximately 69/31% iso to normal ratio) was contacted with chlorine gas (199.2 g, 2.81 mole) over a period of about four hours under photochemical illumination. As before, the ether was contacted with an initial aliquot of about 10 g chlorine gas and illuminated until the color of the chlorine gas had vanished before proceeding with the rest of the addition.

GLC at the conclusion of the addition showed the following: $C_4F_9OCH_3$ (5%), $C_4F_9OCH_2Cl$ (65%) and $C_4F_9OCHCl_2$ (29%) and $C_4F_9OCHCl_3$ (0.2%). The reaction solution was washed first with dilute aqueous potassium hydroxide, and then with water, and distilled using a 40-plate perforated plate column to yield $C_4F_9OCH_2Cl$, b.p.=87° C. and $C_4F_9OCHCl_2$, b.p.=96° C. in purities of about 99%.

Example 3

Preparation of a Mixture of $C_4F_9OCH_2Cl$ and $C_4F_9OCH_2F$

A pressure vessel was charged with $C_4F_9OCH_2Cl$ (75 g, 0.26 mole, isomer ratio i/n=69:31), potassium fluoride (16.8 g, 0.29 mole) and phase transfer catalyst Adogen™ 464 (7 g, methyltrialkyl-C8 to C10 ammonium chloride available from Aldrich Chemical Company), in anhydrous diglyme (150 g) and was heated to 150° C. for slightly more than four hours. The reactor was cooled, water was added, and the contents azeotropically distilled to yield 49.6 grams of reaction product. The reaction product was determined by glc to be a mixture of starting material (68.5%) and the monofluoride (26.%).

Example 4

Preparation of $C_4F_9OCH_2I$ $C_4F_9OCH_2Cl$ (50 g, 0.175 mole, isomer ratio n/i=95:5) was combined with sodium iodide (52.5 g, 0.38 mole) in acetone (200 g) and heated to reflux overnight. Water was added and the acetone distilled from the reaction vessel using a Dean-Stark apparatus. The product was washed with water to remove residual acetone. Glc of the residue (52.6 g) revealed it to be 82.6 wt. % of the desired product $C_4F_9OCH_2I$, which was further purified by distillation. The distillation fraction boiling at 110–115° C. was found to be 97.8 wt. % of the desired product with a 96/4 normal to iso ratio.

Example 5

Preparation of $C_4F_9OCH_2Br$ $C_4F_9OCH_2I$ (31.2 g, 0.081 mole, Example 5) was combined with LiBr in anhydrous dimethyl formamide (100 mL)

and stirred at room temperature overnight. Water was added and the product azeotropically distilled to yield a clear liquid (21.2 g) after separation of the lower aqueous phase and washing with water. This liquid was distilled using a concentric tube column to yield a fraction boiling at 96–97° C., which was revealed by glc to be 97.1 wt. % of the desired compound, $C_4F_9OCH_2Br$ (14.2 g, 67% yield). The structure was confirmed by gc-ms and $^1H$ and $^{19}F$ NMR, which determined that the isomer ratio was about 96/4 normal to iso-$C_4F_9$.

Example 6

Using essentially the procedure of Example 1, perfluorocyclohexylmethyl methyl ether, c-$C_6F_{11}CF_2OCH_3$, containing several other compounds, predominately perfluoromethylcyclopentyl isomers, (134 g, 0.37 mole) was contacted with chlorine gas under UV illumination. Total chlorine was 26.3 g (0.37 mole). The reaction mixture was washed with aqueous KOH, water, and the dried over $Na_2SO_4$ to yield 147 g of product mixture. This was distilled to give a main cut of 141–142° C., which was determined by gcms, $^1H$ and $^{19}F$ NMR to be a mixture of 73% cyclohexyl and 23% methylcyclopentyl isomers and containing both monochloro and dichloro ethers with a ratio of mono to dichloro isomers of 70/30.

Example 7

Preparation of $C_4F_9OCHClCH_3$

Using essentially the procedure of Example 1, $C_4F_9OCH_2CH_3$ (131.2 g, 0.5 mole, isomer ratio n/i=95:5) was contacted with chlorine gas (35.3 g, 0.5 mole) under UV illumination. The reaction mixture was washed with aqueous KOH and dried over $Na_2SO_4$ to yield 140.1 g of clear liquid. The product was distilled using a concentric tube column to give a main fraction boiling at 94° C. to yield the desired compound $C_4F_9OCHClCH_3$, (97% purity, 65% yield with a normal to iso ratio of 94/6). The structure was confirmed by gc-ms, $^1H$ and $^{19}F$ NMR. In addition to the desired product, NMR of a fraction boiling at 113–115° C. was found to contain $C_4F_9OCH_2CH_2Cl$, $C_4F_9OCCl_2CH_3$, $C_4F_9OCH_2CHCl_2$ and $C_4F_9OCHClCH_2Cl$ in the ratio of 49/35/5/11. Four other chlorinated products were identified comprising the remainder of the sample.

Example 8

Preparation of $C_4F_9OCH_2Cl$ and $C_4F_9OCHCl_2$ Using Free Radical Initiator

A flask equipped with a dry ice condenser, mechanical stirrer, gas inlet and thermometer was charged with $C_4F_9OCH_3$ (666 g, 3.33 mole, approximately 9:1 iso to normal) and VAZO 64™ (4 g). The mixture was heated to 60° C. and chlorine bubbled through the stirred solution in small portions. After the addition of 147 g of chlorine, an additional 1 gram of VAZO 64™ was added and heating continued. The reaction mixture was then washed with water and aq $KHCO_3$, and dried over $Na_2SO_4$. GLC of the product mixture revealed $C_4F_9OCH_3$ (24%), $C_4F_9OCH_2Cl$ (62.5%) and $C_4F_9OCHCl_2$ (10.3%)

Example 9

Preparation of cyclo-$C_5F_{10}N(CF_2)_3OCH_2Cl$ and cyclo-$C_5F_{10}N(CF_2)_3OCHCl_2$ The starting material for the chlorination reaction was prepared according to the procedure described in PCT published application No. WO 96/22356, Example 4. The starting material was a mixture of perfluoropiperidinyl (83%); perfluoro-3-methylpyrrolidinyl (9.3%) and perfluoro-2-methylpyrrolidinyl (4.2%) with 3.8% ring-opened aminoether. The remaining 1% were hydride containing materials. Using the procedure of Example 1, perfluoropiperidinylpropyl methyl ether (composition noted above) (28 g=62.9 mmole) was reacted with chlorine (20 g, 281.7 mmole, excess) added in aliquots of about four grams each in the presence of VAZO-64™ (about 0.2 g) at 60° C. The reaction was monitored by glc until the starting material was reduced to about 6% of the reaction mixture. The product was washed with water and distilled using the concentric tube column to afford a product of bp=167° C. $^1H$ and $^{19}F$ NMR revealed the distilled product to be a 70/30 mole ratio of mono to dichlorides.

Example 10

Preparation of 2-trifluoromethyl 3-chloromethoxy perfluoropentane and 2-trifluoromethyl 3-Dichloromethoxy Perfluoropentane The starting material, $C_2F_5COCF(CF_3)_2$, was prepared by the method of Smith et al. J. Am. Chem Soc. 84 4285 (1962) using hexafluoropropylene and pentafluoropropionyl fluoride. A mixture of 2-trifluoromethyl-perfluoro-3-pentanone (105.3 gms. 0.333 moles) in anhydrous diglyme (220 gms), anhydrous potassium fluoride (27.1 gms, 0.467 moles), Adogen ™464(7 gms) and dimethyl sulfate (46.2 gms, 0.37 moles) was heated overnight at 45° C. Upon completion of the reaction, the mixture was cooled and aqueous potassium hydroxide was added slowly to the reaction mixture and stirred for 1 hr at ambient temperature. The pH was found to between 6 and 7. The mixture was heated to azeotropically distill the product from the reaction mixture. The product $(C_2F_5CF(OCH_3)CF(CF_3)_2$, (91.6 gms) was collected and analyzed using glc (97% purity) and used in the subsequent chlorination reaction without further purification.

Into a 100 ml three-necked round bottom flask equipped with a Dry Ice-isopropanol condenser, thermometer, and inlet gas tube was placed 44 gms of 2-trifluoromethyl 3-methoxy perfluoropentane along with a small amount of VAZO 64™ (approx 0.1 gms). The mixture was degassed with dry nitrogen and heated to 70° C. while gaseous chlorine was introduced through the fritted glass gas inlet. A sample was taken after 5 gms of chlorine had been added and was determined by gc/ms to be the starting material and 17% of the desired 2-trifluoromethyl 3-chloromethoxy perfluoropentane. Continued addition of chlorine for a theoretical amount of one mole chlorine per mole of ether gave a mixture of 57% starting material, 37.6% monochloro ether and 3.1% dichloro ether. The product was isolated by quenching the reaction mixture with water, phase separation of the lower product phase, followed by subsequent washing with saturated potassium bicarbonate to yield 50.9 gms of a clear colorless liquid.

Examples 11–13

Compounds of the type $R_fOCF_2CH_2Cl$ were prepared by reaction of the corresponding nonafluorobutanesulfonate ($R_fOCF_2CH_2OSO_2C_4F_9$) with lithium chloride in dimethylformamide as solvent at elevated temperature. The reaction mixture is gently heated until the ether chloride begins to distill from the reaction mixture. The nonafluorobutanesulfonates are prepared by reaction of the corresponding alcohol with nonafluorobutanesulfonyl fluoride in the presence of triethylamine as described in Savu, U.S. Pat. No. 5,550,273 the disclosure of which is herein incorporated by reference.

In this manner the following ether chlorides were prepared.

$C_4F_9OCF_2CH_2Cl$ B. P.=55–56° C.
$CF_3O(C_2F_4O)_2CF_2CH_2Cl$ B. P.=62° C.
$C_6F_{13}OC_2F_4OCF_2CH_2Cl$ B.P.=164–6° C.

Solvency Properties

A number of ethers were tested for their ability to dissolve hydrocarbons of increasing molecular weight, according to the procedure described in U.S. Pat. No. 5,275,669 (Van Der Puy et al.), the description of which is incorporated herein by reference. The data shown in the following table were obtained by determining the largest normal hydrocarbon alkane which was soluble in a particular ether at a level of 50 percent by volume (i.e., 50% by volume hydrocarbon was dissolved in 50% by volume ether). The numbers in the Table correspond with the carbon number of the largest soluble alkane, e.g., "8" refers to octane. Measurements were taken at room temperature and at the boiling point of the ether. The following table summarizes the physical properties and solvency data.

| Compound | Boiling Point | HC Solvency Number at RT and BP | Ozone Depletion Potential |
|---|---|---|---|
| $C_3F_7OCH_2Cl$ | 59.6° C. | 15/20 | 0.013 |
| $C_3F_7OCHCl_2$ | 67.7° C. | 17/>28 | 0.024 |
| i-$C_4F_9OCH_2Cl$ [1] | 87° C. | 13/21 | — |
| i-$C_4F_9OCHCl_2$ [1] | 96° C. | 17/>28 | — |
| cyclo-$C_6F_{11}CF_2OCH_2Cl$ and cyclo-$C_6F_{11}CF_2OCHCl_2$ [2] | 141–142° C. | 12/– | — |
| i-$C_4F_9OCH_2Br$ | 97° C. | 17/– | 0.21 |
| i-$C_4F_9OCH_2I$ | 113° C. | — | — |
| i-$C_4F_9OCHClCH_3$ | 94° C. | 15/– | |
| cyclo-$C_5F_{10}N(CF_2)_3OCH_2Cl$ and cyclo-$C_5F_{10}N(CF_2)_3OCHCl_2$ (70:30) | 144–147° C. | 10/– | |
| $C_4F_9OCF_2CH_2Cl$ | 55–56° C. | 8/– | |
| $CF_3O(C_2F_4O)_2CF_2CH_2Cl$ | 62° C. | 8/– | |

[1] 69% iso-$C_4F_9$ and 31% n-$C_4F_9$
[2] Obtained as a mixture of 73% cyclohexyl and 23% methylcyclopentyl isomers with a ratio mono to dichloro isomers of 70/30.
* Ozone Depletion Potential is described in Scientific Assessment of Stratospheric Ozone: Volume 2, Appendix: AFEAS Report, Section VIII, Ozone Depletion Potentials (1989).

What is claimed is:

1. Perfluoroalkyl haloalkyl ethers having the formula:

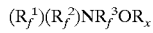

wherein $R_x$ is a haloalkyl; $R_f^1$ and $R_f^2$ are independently straight or branched perfluoroalkyl groups, or, are independently straight or branched perfluoroalkylene groups bonded together to form a ring; $R_f^3$ a linear or branched perfluoroalkylene, and $R_f^1$, $R_f^2$, and $R_f^3$ can optionally and independently contain one or more catenary heteroatoms.

2. The perfluoroalkyl haloalkyl ethers of claim 1, wherein $R_f^1$ and $R_f^2$ are straight or branched perfluoroalkyl groups comprising from 1 to 6 carbons, or are straight or branched perfluoroalkylene groups comprising from 2 to 4 carbons bonded to each other to form a ring, and $R_f^3$ is a linear or branched perfluoroalkylene having from 1 to 6 carbon atoms, wherein $R_f^1$, $R_f^2$ and $R_f^3$ can optionally and independently contain one or more catenary heteroatoms.

3. Perfluoroalkyl haloalkyl ethers of claim 1, having the general formula:

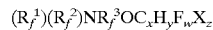

wherein $R_f^1$ and $R_f^2$ are straight or branched perfluoroalkyl groups comprising from 1 to 6 carbons, $R_f^3$ is a linear or branched perfluoroalkylene having from 1 to 6 carbon atoms; x is in the range from 1 to 6; y is at least one; w is in the range from 0 to about 2, X is a halogen chosen from bromine, iodine, and chlorine; z is at least one; and w+y+z is equal to 2x+1.

4. The perfluoroalkyl haloalkyl ethers of claim 3, having the formulas cyclo-$C_5F_{10}N(CF_2)_3OCH_2Cl$ and cyclo-$C_5F_{10}N(CF_2)_3OCHCl_2$.

5. A process for removing contaminants from a substrate, the process comprising the step of contacting the substrate with a composition comprising a perfluoroalkyl haloalkyl ether of claim 1.

6. The process of claim 5, wherein the composition further comprises a surfactant.

7. A coating process comprising the steps of applying to a coating substrate liquid coating composition comprising the perfluoroalkyl haloalkyl ether of claim 1 and at least one coating material which is soluble or dispersible in the perfluoroalkyl haloalkyl ether.

8. The process of claim 7 wherein said coating material is selected from the group of perfluoropolyether, hydrocarbon and silicone lubricants.

9. The process of claim 7 wherein said coating material comprises from about 0.1 to about 10 weight percent of the coating composition.

* * * * *

UNITED STATES PATENT AND TRADEMARK OFFICE
CERTIFICATE OF CORRECTION

PATENT NO. : 6,953,606 B2
APPLICATION NO. : 10/689110
DATED : October 11, 2005
INVENTOR(S) : Frederick E. Behr et al.

It is certified that error appears in the above-identified patent and that said Letters Patent is hereby corrected as shown below:

On the Title Page, in Col. 1, item (62)
Lines 1-2, after "Division of" delete "application No. 09/231,203, filed on Jan. 14, 1999, now".
Line 2, after "6,653,512" delete "," and insert -- ; --, therefor.

Col. 1
Lines 7-8, after "divisional of" delete "application Ser. No. 09/231,203, filed Jan. 14, 1999, now".
Line 8, after "6,653,512" insert -- ; --.

Col. 4
Line 50, in (Structure 4)

insert -- 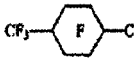 --, therefor.

Col. 5
Line 10, in (Structure 9) (Including Equations)

insert -- 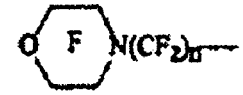 --, therefor.

Lines 14-15, in (Structure 11) (Including Equations)

insert --  --, therefor.

UNITED STATES PATENT AND TRADEMARK OFFICE
CERTIFICATE OF CORRECTION

PATENT NO. : 6,953,606 B2
APPLICATION NO. : 10/689110
DATED : October 11, 2005
INVENTOR(S) : Frederick E. Behr et al.

It is certified that error appears in the above-identified patent and that said Letters Patent is hereby corrected as shown below:

Col. 6
Line 4, in (Formula 1) delete " $CF_3CF_2CF_2OCH_2Cl_2$" and insert
-- $CF_3CF_2CF_2OCH_2Cl$ --, therefor.

Line 6, in (Formula 5) delete "$CF_3CF_2CF_2CF_2OCH_2Cl_2$" and insert
-- $CF_3CF_2CF_2CF_2OCH_2Cl$ --, therefor.

Col. 7
Line 25, after "and" delete "$R_f$" and insert -- $R_f'$ --, therefor.
Line 44, delete "KF.2HF" and insert -- KF2HF --, therefor.

Col. 9
Line 62, delete "nonwoven" and insert -- non-woven --, therefor.

Col. 13
Line 60, after "(10.3%)" insert -- . --.

Col. 16
Line 4, in Claim 1, insert -- is -- before "a linear".

Signed and Sealed this

Thirteenth Day of May, 2008

JON W. DUDAS
*Director of the United States Patent and Trademark Office*